(12) United States Patent
Hummelink (10) Patent No.: US 9,763,748 B2
(45) Date of Patent: Sep. 19, 2017

(54) ANATOMICAL IMAGE PROJECTION SYSTEM

(71) Applicant: Stichting Katholieke Universiteit, Nijmegen (NL)

(72) Inventor: Stefan Laurentius Maria Hummelink, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 0 days.

(21) Appl. No.: 15/125,200

(22) PCT Filed: Mar. 11, 2015

(86) PCT No.: PCT/EP2015/055065
§ 371 (c)(1),
(2) Date: Sep. 12, 2016

(87) PCT Pub. No.: WO2015/135985
PCT Pub. Date: Sep. 17, 2015

(65) Prior Publication Data
US 2017/0165028 A1    Jun. 15, 2017

(30) Foreign Application Priority Data

Mar. 12, 2014 (NL) ..................... 2012416

(51) Int. Cl.
*A61B 90/00* (2016.01)
*A61B 34/20* (2016.01)
(Continued)

(52) U.S. Cl.
CPC ............ *A61B 90/36* (2016.02); *A61B 8/5261* (2013.01); *A61B 34/20* (2016.02); *A61B 90/39* (2016.02);
(Continued)

(58) Field of Classification Search
CPC ......... A61B 90/36; A61B 90/39; A61B 34/20; A61B 8/5261; A61B 2034/2051;
(Continued)

(56) References Cited

U.S. PATENT DOCUMENTS

| | | |
|---|---|---|
| 2012/0008741 A1 | 1/2012 | Hendriks |
| 2012/0188352 A1 | 7/2012 | Wittenberg |
| 2013/0218024 A1 | 8/2013 | Boctor et al. |

FOREIGN PATENT DOCUMENTS

| | | |
|---|---|---|
| EP | 1695670 A1 | 8/2006 |
| EP | 2438880 A1 | 4/2012 |

*Primary Examiner* — Michael Teitelbaum
(74) *Attorney, Agent, or Firm* — NLO N.V.; Catherine A. Shultz; Minerva Rivero (57) ABSTRACT

Projection system for image projection of anatomical features on a subject. Intraoperative position markers (10) are disposed on a first body surface (6), and a moveable first detector (12) with a detection line of sight is provided. A control unit (14) is arranged for registering detected intraoperative position markers (10) with a plurality of preoperative position markers (4) in preoperative images. A movable projector (16) is provided for projecting an image representation (18) of the one or more anatomical features of interest. The projection line of sight is substantially parallel to the detection line of sight. The control unit (14) is in communication with the first detector (12) and projector (16) and arranged for real-time image projection of the image representation (18) on the second body surface (20) by the projector (16) independent from synchronized movement and varying detection/projection angles of the first detector (12) and the projector (16).

21 Claims, 3 Drawing Sheets

(51) Int. Cl.
*A61B 8/08* (2006.01)
*H04N 9/31* (2006.01)

(52) U.S. Cl.
CPC ......... *H04N 9/3161* (2013.01); *H04N 9/3194* (2013.01); *A61B 2034/2051* (2016.02); *A61B 2034/2055* (2016.02); *A61B 2090/363* (2016.02); *A61B 2090/366* (2016.02); *A61B 2090/3937* (2016.02); *A61B 2090/3979* (2016.02)

(58) Field of Classification Search
CPC ...... A61B 2034/2055; A61B 2090/363; A61B 2090/366; A61B 2090/3937; A61B 2090/3979; H04N 9/3194; H04N 9/3161
See application file for complete search history.

ANATOMICAL IMAGE PROJECTION SYSTEM

FIELD OF THE INVENTION

The present invention relates to an anatomical image projection system, more particularly to an anatomical image projection system for image projection of anatomical features on a body surface of a subject.

In a further aspect the present invention relates to a method for image projection of anatomical features on a body surface of a subject.

PRIOR ART

European patent application EP 1 695 670 A1 discloses a portable laser projection system suitable for anatomical image projection on a subject, comprising a movable handheld laser projector and a separate navigation system comprising one or more tracking camera's and reference markers. In an embodiment the handheld laser projector comprises a navigation reference.

The prior art handheld laser projector has the disadvantage of requiring a separate navigation system provided with a tracking camera and reference markers for projecting an anatomical image onto a subject.

European patent application EP 2 438 880 discloses a handheld projector device, wherein the projector is provided with position markers to be observed with a separate position sensor. The projector may be seen as a virtual camera, wherein the virtual camera's position is determined from inverting the projector's projection parameters.

US patent application US 2012/0188352 discloses a projection device for superimposing an intraoperative first live image of an operating field with a preoperative second image of the operating field. A projector and monitor may be provided for showing a live image of the operating field utilizing intraoperative position markers. The camera may be associated with an endoscope.

US patent applications US 2012/008741 and US 2013/218024 each disclose a anatomical projection device wherein a camera and projector may be mounted on a single C-frame.

SUMMARY OF THE INVENTION

The present invention seeks to provide an improved anatomical image projection system for projecting one or more image representations of anatomical features of interest on a body surface of a subject, wherein the projection system comprises a movable detector and movable projector configured for projecting an image representation of one or more anatomical features onto a subject independent from synchronous movement of said detector and projector.

According to the present invention, an anatomical image projection system according to the preamble is provided, comprising a plurality of intraoperative position markers removably disposed on a first body surface; a moveable first detector for intraoperative detection of the plurality of intraoperative position markers and having a detection line of sight; and a control unit arranged for receiving one or more preoperative images comprising one or more anatomical features of interest, each of the preoperative images comprising a plurality of preoperative position markers, wherein the control unit is further arranged for registering the detected plurality of intraoperative position markers with the plurality of preoperative position markers in each of the preoperative images; the projection system further comprising a movable projector having a projection line of sight and being configured for projecting an image representation of the one or more anatomical features of interest on a second body surface, the projection line of sight being substantially parallel to the detection line of sight, the projected image representation being based on the one or more preoperative images and the registered plurality of intraoperative position markers and the plurality of preoperative position markers, wherein the control unit is in communication with the first detector and projector and arranged for real-time image projection of the image representation on the second body surface by the projector independent from synchronized movement of the first detector and the projector.

It is noted that the terms first body surface and second body surface are used herein to denote the possibility of two instances in time, and in fact the first body surface and second body surface may coincide. It is further noted that the first and/or second body surface are typically not flat surfaces and comprise a three dimensional profile (e.g. upstanding walls, recesses etc.) following body and organ curvatures and the like. The projected image representation of the present invention is therefore three dimensional in nature, wherein said projected representation is adapted accordingly to the three dimensional profile. This may be detected by an appropriate first detector embodiment, e.g. in the form of a time-of-flight camera, stereoscopic camera, etc.

The present invention has the advantage of avoiding statically positioned detectors and/or projectors for projecting the image representation on a body surface of a subject. Steady and accurate alignment as well as image focus of the projected image representation is ensured even when the first detector and the projector are moving in unison or synchronicity with respect to the subject. Also, steady and accurate alignment as well as image focus of the projected image representation is ensured when the subject is moving instead of the first detector and the projector.

According to the present invention embodiments, relative motion between the subject and the first detector and projector has no negative impact on steady and accurate alignment as well as image focus of the projected image representation. In particular, the projected image representation of the one or more anatomical features shows very little to no discernible shift parallel to the surface on which it is projected during relative motion between the subject and the first detector and projector, e.g. the first and/or second body surface. The projection system of the presenting invention compensates for relative motion between the subject, such as the first and/or second body surface, and the first detector and projector, thereby ensuring accurate alignment of the projected image representation whenever the subject is moving and/or the first detector and projector are moving. As a result, time consuming and complicated calibration procedures are avoided.

The projection system according to the invention needs no special features such as separate navigation and detection systems and allows for a portable detection and projection solution. The projection system provides static or dynamic projection independent from shared detection and projection movement such as upward, downward and/or rotational movements. A further advantage of the present invention is that only a plurality of intraoperative position markers are required disposed on a body surface of the subject. No other reference/position markers or separate navigation and reference systems are needed. This avoids stationary, bulky, and often complex equipment supporting the detector and/or the projector, which is particularly advantageous in e.g. operating rooms.

In an embodiment, the projected image representation is a static (steady) image projection. This embodiment provides a statically projected image representation of the one or more anatomical features independent from synchronized movement of the first detector and the projector.

In a further embodiment, the projection system further comprises a second detector configured for intraoperative detection of motion of the subject, wherein the control unit is in further communication with the second detector and arranged for dynamically projecting the image representation in real-time, the projected image representation comprising the motion of the one or more anatomical features of interest.

In an embodiment the second detector may be the same detector as the first detector, with added functionality of extraction of motion in the received images. This embodiment reduces the complexity of the projection system as the control unit only communicates with a single detector, i.e. the first and second detector being the same physical detector.

In an advantageous embodiment, the first detector and the projector are disposed in a portable handheld housing for synchronous movement. This embodiment is particular advantageous as a user of the projection system may hold the detector and projector in one hand without influencing or compromising the quality of the projected image representation of the one or more anatomical features of interest. For example, in medical procedures a surgeon or a general user may hold the handheld detector and projector and show a projected image to a subject and explain particular anatomical features and/or characteristics of a procedure in further detail. Alternatively, the handheld housing comprising the detector and projector may also be used for educational purposes in a myriad of ways, showing detected (anatomical) features to students or patients. In any case, the handheld portable embodiment of the projection system may be used for various medical and non-medical applications.

In an even further embodiment, the projection system comprises a second detector configured for intraoperative detection of motion of the subject (e.g. heart and/or breathing motion), wherein the control unit is in further communication with the second detector and arranged for dynamically projecting the projected image representation in real-time, the projected image representation comprising the motion of the one or more anatomical features of interest.

In an embodiment, the projector is a laser projector, which has the advantage of always providing a focussed projected image representation. As an alternative, any projector maintaining focus over a predetermined projection distance may be used (e.g. LED projector).

In an embodiment, the control unit is further arranged to stop (or discontinue) image projection of the image representation when one or more intraoperative position markers lie outside a predetermined range of the detection line of sight of the first detector. This embodiment may be advantageous to prevent projection when e.g. the first detector and projector are pointed away from the subject, or the subject itself blocks detection of one or more intraoperative position markers.

In a further embodiment, the control unit is arranged to stop image projection of the image representation when each of the plurality of intraoperative position markers are in the detection line of sight of the first detector, and wherein the detection line of sight lies outside a predetermined detection range. This embodiment only allows image projection of the one or more anatomical features of interests for a predetermined detection range for the detection line of sight, i.e. when the first detector has a particular position and orientation/angle that lies within this predetermined range. In this way selective projection is made possible within the predetermined range whereas outside this range image projection is stopped. This embodiment may be advantageous for e.g. "key hole" projections in which one or more anatomical features of interest are projected if and only the first detector detects the subject from a relatively small or narrow detection range of particular positions and angles, hence the name "key hole".

In a further embodiment, the control unit is arranged to stop image projection of the image representation when each of the plurality of intraoperative position markers are in the detection line of sight of the first detector, and when a secondary anatomic feature is interposed between the one or more anatomic features to be projected and the first detector along the detection line of sight thereof.

This embodiment may also be advantageous for "key hole" projections in which one or more anatomical features of interest are projected if and only if said anatomical features of interest are readily accessible in a restricted predetermined region or range of the detection line of sight of the first detector. Such a scenario may occur, for example, for one or more anatomical features of interest surrounded by secondary anatomical features blocking access (e.g. nerve bundles, fat structures and the like).

Note that in further embodiments a plurality of the above mentioned "key hole" projections may also be envisaged, thus wherein one or more anatomical features of interest are projected if and only if the detection line of sight of the first detector lies within one of a plurality of predetermined detection ranges.

In all of above mentioned embodiments, stopping image projection for positions and/or angles of the first detector outside one or more predetermined detection ranges may improve safety, minimize erroneous projections, and/or when such projections make sense in view of an orientation of the subject and the first and/or second body surface.

In a further aspect, the present invention seeks to provide an improved method for image projection of anatomical features on a subject, the method comprises providing one or more preoperative images of one or more anatomical features of interest using a medical imaging apparatus, each of the preoperative images comprising a plurality of preoperative position markers; storing the one or more preoperative images into an image storage unit; post processing the stored one or more preoperative images into one or more image representations comprising simplified images or views (e.g. filtered, selective of schematic images or views) of the one or more anatomical features of interest; disposing a plurality of intraoperative position markers on the first body surface of the subject at the same location as the plurality of preoperative position markers; detecting the plurality of intraoperative position markers intraoperatively using a movable first detector having a detection line of sight; registering the detected plurality of intraoperative position markers with the plurality of preoperative position markers in each of the one or more image representations; projecting substantially parallel to the detection line of sight the one or more image representations on a second body surface intraoperatively using a movable projector having a projection line of sight, wherein projecting the one or more image representations comprises real-time projection independent from synchronized movement of the first detector and the projector.

The method of the present invention has the advantage of allowing for detection and projection independent from shared or synchronous detection and projection directions, thereby providing greater flexibility without sacrificing detection and projection accuracy. The method of the present invention is particular advantageous for mobile and portable applications, wherein detection and projection is generally accomplished through synchronous or "in sync" movements.

Advantageously, in an embodiment the method may further comprise detecting motion of the subject using a second detector, dynamically projecting the one or more image representations comprising the motion of the one or more anatomical features of interest in real-time.

SHORT DESCRIPTION OF DRAWINGS

The present invention will be explained in further detail hereinafter based on a number of exemplary embodiments with reference to the drawings, wherein.

DETAILED DESCRIPTION OF EXEMPLARY EMBODIMENTS

In plastic surgery, such as breast reconstruction using deep inferior epigastric perforators (DIEP) flap reconstruction, wherein skin and fat from the lower abdominal region may be transferred to the breast area for reconstructing a breast following a mastectomy. Once a so-called "flap" comprising skin, various tissues and perforators from the lower abdominal region has been excised, the "flap" is transplanted and connected to a subject's breast region. This surgical procedure is often referred to as "DIEP-flap".

Even though the above procedure is conceptually straight forward, various difficulties arise in regard to localising the required blood vessels and perforators in the abdominal fascia. Typically a Doppler system is utilised for localising the blood vessels in the lower abdominal region, but this is time consuming and rather inaccurate. Also, the amount of information received from the Doppler system is relatively limited.

For these and various other surgery procedures, there has been a long felt need for an anatomical image projection system and method capable of statically or dynamically projecting one or more image representations of one or more anatomical features onto a subject. This has mostly resulted in complex and bulky system solutions, which are not very efficient and easy to use in e.g. an operating room. The present invention provides a projection system and method as claimed in the independent claims, and further embodied in the dependent claims, which can operate independently and in an easy manner as a handheld unit, without needing any further positioning or navigation system (in the operating theatre).

Figure 1:
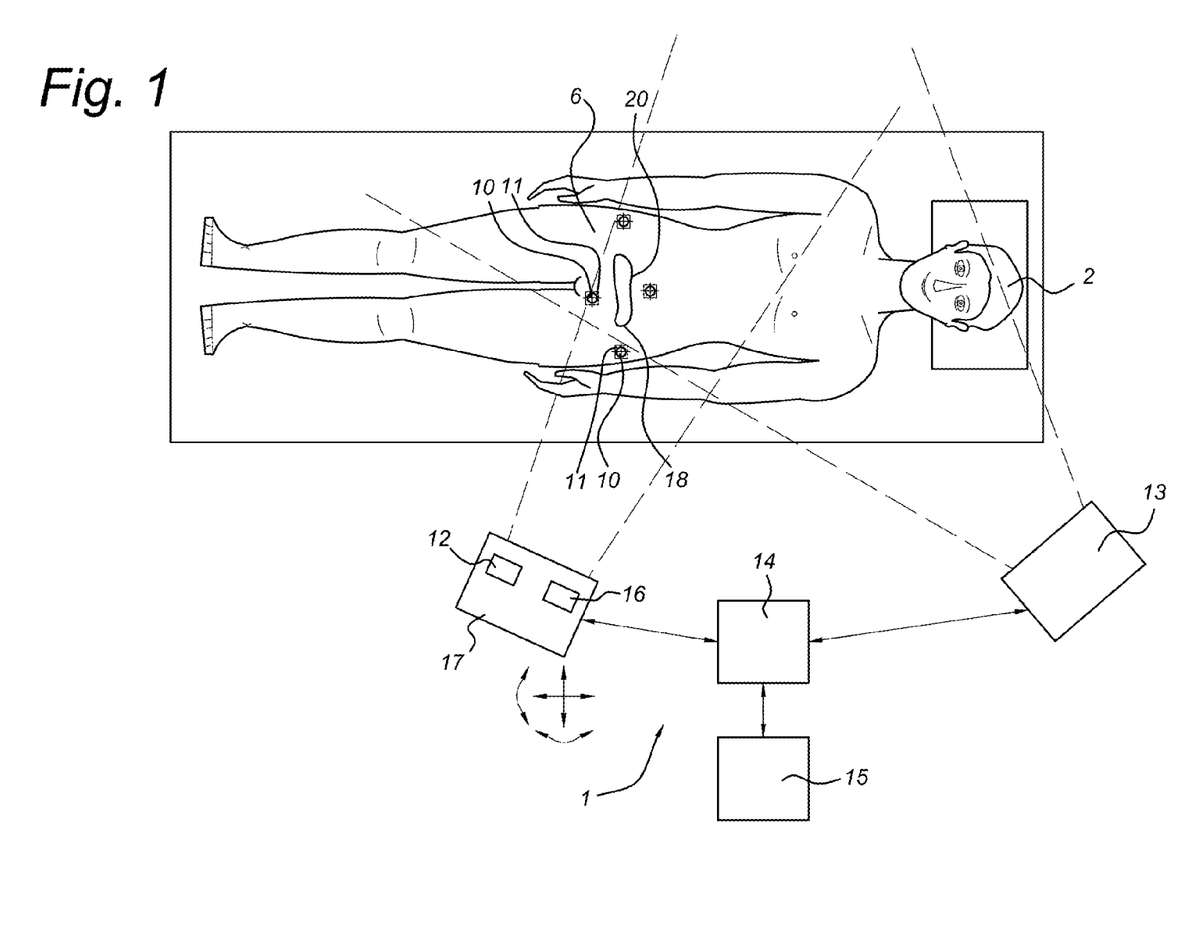
FIG. 1 shows an embodiment of the anatomical image projection system according to the present invention.

FIG. 1 depicts an anatomical image projection system 1 according to the present invention, comprising a plurality of intraoperative position markers 10 removably disposed on a first body surface 6 of a subject 2. The plurality of intraoperative position markers 10 are needed for facilitating correct projection and image alignment as wells as orientation on the first body surface 6. In advantageous embodiments the projection system 1 comprises at least three intraoperative position markers 10 to accurately show and distort/adapt an image for projection.

Typically, the first body surface 6 is skin surface of the subject 2. The first body surface 6 may also be an internal body surface of a subject in certain applications of the projection system 1.

The projection system 1 further comprises a moveable first detector 12 for intraoperative detection of the plurality of intraoperative position markers 10 within a detection line of sight. In an embodiment, the first detector 12 may be a digital camera of which the detection line of sight is directed to a region having a plurality of intraoperative position markers 10, wherein each of said intraoperative position marker 10 is a visual position marker. In another embodiment the first detector 12 may be an infra camera and each of the plurality of intraoperative position markers 10 may comprise a heat or cold source. This embodiment is advantageous in e.g. dark environments, where the plurality of intraoperative markers 10 are distinguishable by their temperature different from their surrounding area. In yet another embodiment the first detector 12 may be an RFID receiver and each of the plurality of intraoperative position markers 10 may comprise an RFID transmitter. This embodiment is particularly advantageous in situations where a largest detection line of sight or detection horizon is required.

It is noted that in case of an RFID receiver (first detector 12), the detection line of sight is interpreted as a general direction, such that the plurality of intraoperative position markers 10 are in a reception field of view of the RFID receiver 12.

In further embodiments, the plurality of intraoperative position markers 10 may be markers in an anatomical sense, such as body surface and/or bone features. Then the associated first detector 12 is e.g. a (Time of Flight) camera or even an ultrasound (Doppler) system detecting the body surface and/or bone features through e.g. surface matching and/or anatomical markers obtained by ultrasound (echo).

Figure 2:
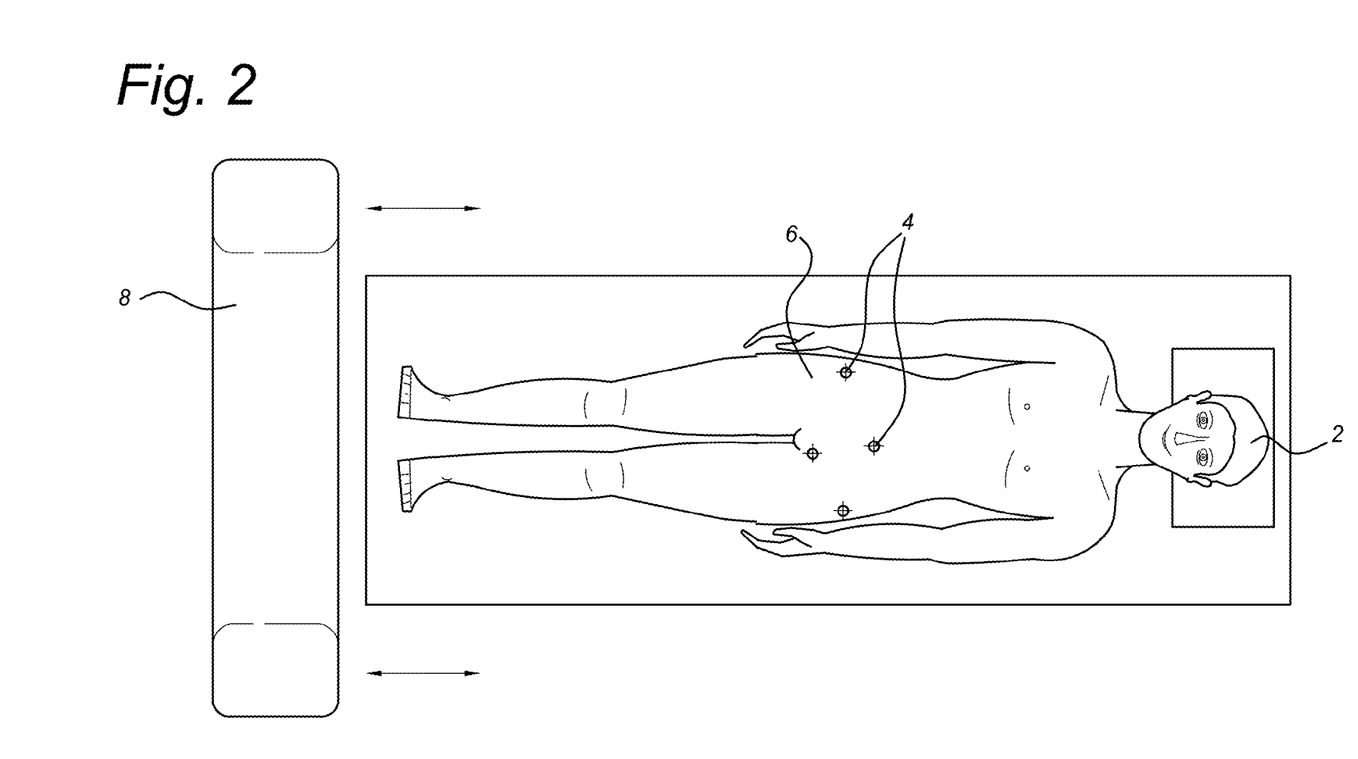
FIG. 2 shows an embodiment of a preoperative arrangement of position markers on a subject according to the present invention.

As depicted, the projection system 1 is further provided with a control unit 14 arranged for receiving one or more preoperative images comprising one or more anatomical features of interest, wherein each of the one or more preoperative images comprises a plurality of preoperative position markers 4. FIG. 2 depicts an exemplary setup on how one or more preoperative images may be obtained, wherein the one or more anatomical features and plurality of preoperative position markers 4 may be imaged using a medical imaging apparatus 8 (e.g. CT, MRI).

The one or more preoperative images of anatomical features of interest need not only comprise anatomical features to be projected but may also comprise secondary or further anatomical features to facilitate image processing as well as more accurate image projections at a particular moment in time. Also, these secondary anatomical features may be used to map a surrounding volume of anatomical features to be projected, so that the accessibility of the projected feature is analysed and estimated.

In light of the present invention it is conceivable that the one or more preoperative images may comprise, or may be combined, to obtain a partial or complete 3D model of a subject 2 comprising a host of anatomical features that may be helpful in providing more accurate and reliable image projections as well as information about the immediate vicinity of a projected anatomical feature. Examples of secondary anatomical features may be further bone structures, muscle and tendon structures, fat structures and layers thereof, blood vessels, lymph nodes, nerve bundles of the central and/or peripheral nervous system, etc.

The plurality of preoperative position markers 4 are typically disposed on the first body surface 6 (e.g. skin tissue) and provide location information of the one or more anatomical features as imaged by the medical imaging apparatus 8 with respect to the subject 2. The plurality of preoperative position markers 4 then facilitate alignment of a projected image by the projection system 1 onto the subject 2 with respect to a physical location of the one or more anatomical features of the subject 2. The plurality of preoperative position markers 4 may further facilitate alignment of an imaged 3D model with respect to the subject 2 to support accurate projections of one or more anatomical features as well as accessibility information pertaining thereto. In case the plurality of preoperative position markers 4 are used with e.g. a CT scanner, said plurality of preoperative position markers 4 typically comprise parts made of lead for optimal image capture of said markers 4 onto the one or more preoperative images. On other embodiments, the plurality of preoperative position markers 4 may be physiological markers such as bone structures of the subject, e.g. pelvic bone structure and the like. Hence, according to the invention, the plurality of preoperative position markers 4 may be externally applied position markers or may be physiological markers/characteristics of the subject such as bone or tissue structures scanned by e.g. a CT or MRI scanner.

The projection system 1 may comprise a storage unit 15 in communication with the control unit 14 for collectively storing the one or more preoperative images. The storage unit 15 need not be part of the projection system 1 as long as an external storage unit 15 is configured to communicate with the control unit 14 for exchanging image data.

In the embodiment shown in FIG. 1, the control unit 14 is further arranged for registering the detected plurality of intraoperative position markers 10 with the plurality of preoperative position markers 4 in each of the preoperative images. That is, the control unit 14 is arranged for aligning the detected plurality of intraoperative position markers 10 with the plurality of preoperative position markers 4 shown in the one or more preoperative images. In this way a correct position and orientation of a projected image as well as a (partial) 3D model of a subject can be ensured. Such a correct position and orientation of a projected image can already be achieved when the projection system 1 comprises at least three intraoperative position markers 10 (using triangulation detection methods). Note that the plurality of intraoperative position markers 10 are typically disposed at the same location as the plurality of preoperative position markers 4 for optimal alignment of the one or more preoperative images with respect to the first body surface 6, i.e. the plurality of intraoperative position markers 10.

The projection system 1 according to the invention further comprises a movable projector 16 having a projection line of sight and which is configured for projecting an image representation 18 of the one or more anatomical features of interest on a second body surface 20 substantially parallel to the detection line of sight. Hence, both the first detector 12 and projector 16 "point" in a substantially identical direction.

In typical applications of the projection system 1, the second body surface 20 may be an internal body surface such as an abdominal wall (fascia), e.g. in case of the DIEP-flap procedure. Note that the second body surface 20 may also coincide with the first body surface 6, which is sometimes the case in the beginning of a (surgical) procedure. The second body surface 20 may then change to an internal body surface intraoperatively.

The projected image representation 18 is based on the one or more preoperative images and the registered plurality of intraoperative position markers 10 with the plurality of preoperative position markers 4. Since the preoperative and intraoperative markers are registered/aligned by the control unit 14, the projected image representation 18 of the one or more anatomical features is accurate and provides reliable feedback to e.g. a surgeon or general user using the projection system 1.

According to the invention, the control unit 14 is in communication with the first detector 12 and projector 16 and is arranged for real-time image projection of the image representation 18 on the second body surface 20 by the projector 16, independent from synchronized movement of the first detector 12 and the projector 16.

Steady, accurate alignment and focussed image projection of the image representation 18 is ensured even when the first detector 12 and the projector 16 are moving in unison or synchronicity with respect to the subject 2 while projecting the image representation 18. Also, steady, accurate alignment and focussed image projection of the image representation 18 is ensured when the subject 2 is moving instead of the first detector 12 and projector 16. So according to the present invention relative motion between the subject 2 and the first detector 12 and projector 16 does not interfere with steady, accurate alignment as well as focussed image projection of the image representation 18.

The projection system 1 of the invention is therefore capable of providing an accurate projected image appearing without visible visual delay between detection and projection. Note that the phrase "real-time image projection" should thus be construed as projecting an image without noticeable or discernible delay with respect to detection of the plurality of intraoperative position markers 10 and projecting an image representation 18 of the one or more anatomical features onto the subject 2.

In an embodiment, the projected image representation 18 is a steady or static image of one or more anatomical features independent from synchronized movement of the first detector 12 and the projector 16. This embodiment is advantageous as it is now possible to project a static/steady image representation 18 of the one or more anatomical features independent from a shared detection and projection angle (direction) of the first detector 12 and the projector 16. From this it immediately follows that both the first detector 12 and the projector 16 need not be stationary disposed inside e.g. an operating room. Fixed mount points for the projection system 1 are thus avoided, rendering the projection system 1 mobile and hence extremely versatile. In light of this, in an embodiment the first detector 12 and the projector 16 are disposed in a portable handheld housing 17. The housing 17 may take the form of a simple webcam or any other handheld detection device. According to the invention, moving the housing 17 does not interfere with the statically projected image representation 18.

As an alternative to a portable handheld housing 17, in advantageous embodiments the first detector 12 and projector 16 may be disposed in a portable head mount 17 for freeing both hands of a user operating the projection system 1. The portable head mount 17 may also be further provided with (integrated) glasses configured for providing a three dimensional (3D) image of the projected representation 18. In particular, the glasses may comprise an active shutter system for generating a 3D image, wherein the active shutter system utilizes position information of the portable head mount 17 itself inferred from the detected plurality of intraoperative position markers 10.

In an advantageous embodiment of the projection system, the control unit 14 is further arranged to stop image projection of the image representation 18 when one or more intraoperative position markers 10 lie outside a predetermined range of the detection line of sight of the first detector 12. For example, in case the first detector 12 and projector 16 point in a direction away from the subject 2, i.e. pointing away from the plurality of intraoperative position markers 10, then the control unit 14 may stop image projection in that direction. This embodiment may also stop image projection in case the subject 2 blocks detection of one or more intraoperative position markers 10 by the first detector 12. More specifically, the first detector 12 and projector 16 may in fact point toward the subject 2 but accurate image projection cannot be guaranteed as one or more intraoperative position markers 10 lie outside the detection line of sight as the subject 2 itself blocks detection of one or more intraoperative position markers 10.

From a practical point of view this scenario can be envisaged when the first detector 12 and projector 16 point to, for example, a left side of the subject 2 whereas an image representation 18 should be projected onto the right side of the subject 2. In such a scenario one or more intraoperative position markers 10 may "disappear" behind the subject 2 and accurate image projection is not possible.

In a further advantageous embodiment the control unit 14 is arranged to stop image projection of the image representation 18 when each of the plurality of intraoperative position markers 10 are in the detection line of sight of the first detector 12 and wherein the detection line of sight lies outside a predetermined detection range. This embodiment only allows for image projection for a restricted range of positions and orientations/angles of the first detector 12. This predetermined range can be made arbitrarily small or narrow so that the projector 16 only projects anatomical features when the first detector 12 detects the subject 2 through a "key hole" whilst all intraoperative position markers 10 are detected by the first detector.

A more complicated scenario occurs when each one of the plurality of intraoperative position markers 10 is in the detection line of sight of the first detector 12 but one or more anatomical feature to be projected are physically blocked from access by secondary or further anatomical features along the detection line of sight. For example, a sensitive nerve bundle may be interposed between the one or more anatomical features to be projected and the first detector 12. To prevent nerve damage during a possible intervention, the control unit 14 may only allow projection of the image representation 18 not only when each of the plurality of intraoperative position markers 10 are detectable but also when the one ore more anatomical features to be projected are readily accessible in a predetermined detection range along the detection line of sight of the first detector 12.

In view of the above, in a further embodiment the control unit 14 is arranged to stop or discontinue image projection of the image representation 18 when each of the plurality of intraoperative position markers 10 is in the detection line of sight of the first detector 12 and when a secondary anatomic feature is interposed between one or more anatomic features to be projected and the first detector 12 along the detection line of sight thereof.

This embodiment is also suitable for "key hole" projections, thus only projecting an image representation 18 for a predetermined range of positions and/or orientations of the first detector 12 when all intraoperative position markers 10 are in fact detectable by the first detector 12.

In a further advantageous embodiment, the projection system 1 further comprises a second detector 13 configured for intraoperative detection of motion of the subject 2, wherein the control unit 14 is in further communication with the second detector 13 and arranged for dynamically projecting the image representation 18 in real-time, the projected image representation 18 comprising the motion of the one or more anatomical features of interest. This embodiment allows for projection of motion of anatomical features, such as moving abdominal fascia, providing even more accurate feedback on the physical location of the one or more anatomical features.

In a more specific embodiment, the projection system 1 comprises a second detector 13 configured for intraoperative detection of heart and/or breathing motion of the subject 2, wherein the control unit 1 is in further communication with the second detector 13 and arranged for dynamically projecting the projected image representation 18 in real-time, the projected image representation 18 comprising heart and/or breathing motion of the one or more anatomical features of interest.

In a DIEP-flap procedure, for example, the above embodiment would take into account motion of blood vessels and perforators in the lower abdominal region due to heart motion and/or breathing motion. This provides optimal feedback to a surgeon on the physical location of anatomical features of interest.

In a further inventive example, the projection system 1 of the present invention may also be used for real-time organ tracking through ultrasound (Doppler) and by co-imaging an organ of interest and the plurality of intraoperative position markers 10. An organ of interest could be a liver, kidney, heart etc. The plurality of intraoperative position markers 10 are stationary disposed on the first and/or second body surface 6,20 near the organ (e.g. liver, kidney). Ultrasound images showing "live" breathing and/or heartbeat motion of the organ are then associated with corresponding CT images that are projected at the correct location.

According to the invention, the projector 16 may be a laser projector, wherein the laser projector is capable of always providing a focussed projected image representation 18 independent from the distance of the laser projector 16 with respect to the second surface of the subject 2. As a laser projector 16 can be manufactured in a small form factor, the laser projector 16 is very suitable for hand held applications of the projection system 1.

As shown in FIG. 1, the projection system 1 may further comprise a separate surface patch 11 for each of the plurality of intraoperative position markers 10, wherein each separate surface patch 11 is removably disposed on the first body surface 6. In practical terms each surface patch 11 may take the form of a sticker patch 11 that is easily removed without discomfort to the subject 2. Having a separate surface patch 11 for each of the intraoperative position markers 10 is advantageous as it provides more freedom of placement of said position markers 10.

Alternatively, the projection system 1 may further comprise a single surface patch 11 provided with the plurality of intraoperative position markers 10, the surface patch 11 being removably disposed on the first body surface 6. In this embodiment, the surface patch 11 may take the form of e.g. a sticker patch. In this particular embodiment it may be needed to have an opening in the surface patch 11 for exposing the second body surface 20 on which the image representation 18 of the one or more anatomical features is to be projected.

For optimal registration of the plurality of intraoperative and preoperative position markers 10,4 by the control unit 14, each of the intraoperative position markers 10 may comprise a plurality of polygon markers, such as rectangular and/or square bar markers. Such polygon markers provide sufficient contrast to be detected by the first detector 12. It would even be possible to use body surface features (e.g. navel or distinct bone parts or bone ends, etc.) in one or more intraoperative position markers 10 for optimal registration of the plurality of intraoperative and preoperative position markers 10,4.

Figure 3:
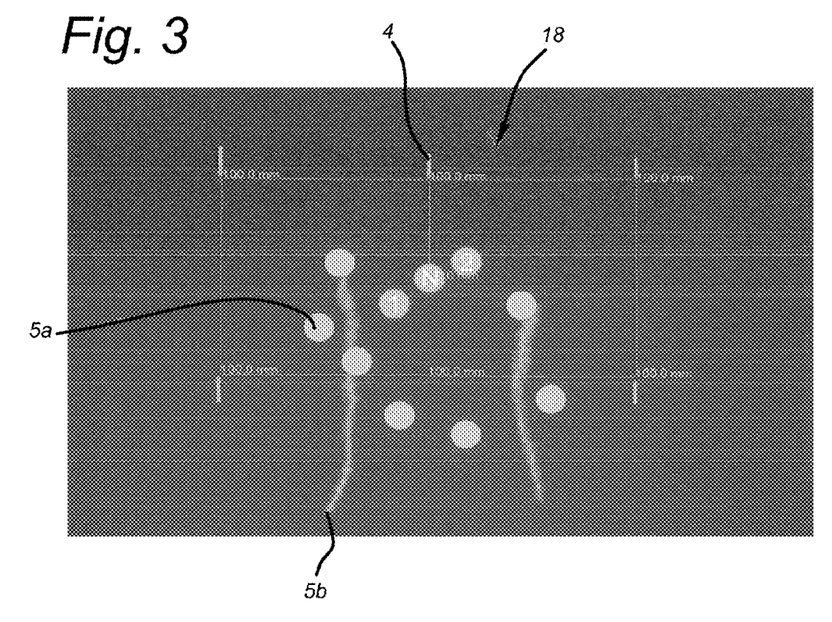
FIG. 3 shows an embodiment of an image representation of one or more anatomical features of interest according to the present invention.

FIG. 3 depicts an embodiment of a projected image representation 18 of the one or more anatomical features 5a, 5b of interest, wherein a plurality of preoperative position markers 4 are depicted enclosing the one or more anatomical features such as perforators 5a and blood vessels 5b. The projection system 1 of the present invention projects such an image representation 18 of the one or more anatomical features onto the subject 2, wherein the control unit 14 registers the plurality of preoperative position markers 4 with the plurality of intraoperative position markers 10 as shown in FIG. 1. In the embodiment shown, the projected image representation 18 comprises a flat view of anatomical features. In other embodiments, the projected image representation 18 may comprise a perspective view of anatomical features in case a field of depth is to be projected.

Figure 4:
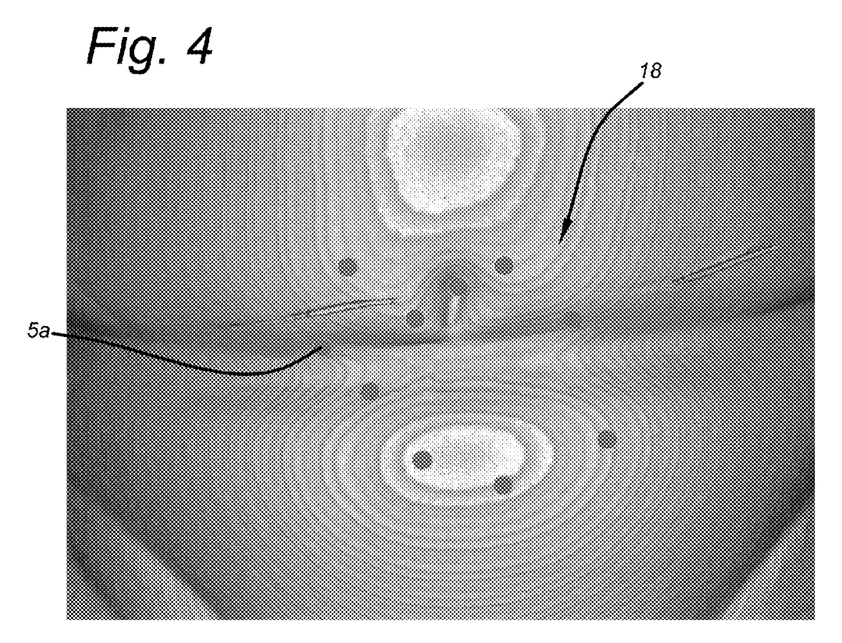
FIG. 4 shows an embodiment of a projected image representation of one or more anatomical features of interest on a subject according to the present invention.

FIG. 4 depicts another embodiment of a projected image representation 18 of one or more anatomical features 5a, 5b of interest onto a second body surface 20. The second body surface 20 may comprise an outer body surface such a skin surface or comprises an internal body surface such as abdominal fascia.

In aforementioned paragraphs it is disclosed that the projection system 1 comprises a control unit 14 arranged for receiving one or more preoperative images comprising one or more anatomical features of interest as well as secondary anatomical features for facilitating image processing and image projection. According to the invention, the one or more anatomical features may comprise "raw" anatomical feature information as directly provided by, for example, a medical imaging apparatus 8 (e.g. CT, MRI). It is then be possible to project an image representation 18 of the one or more anatomical features in such a "raw" format, projecting all anatomical features as captured by the medical imaging apparatus 8. The term "raw anatomical feature information" should thus be construed as unfiltered or non-processed anatomical feature information obtained from a medical imaging apparatus 8.

Projection of raw anatomical feature information onto a subject 2 may not be suitable in certain situations as there may be too much information in each of the one or more preoperative images, thereby cluttering and masking one or more anatomical features relevant to the application at hand.

In advantageous embodiments of the projection system, the one or more preoperative images may be post-processed preoperative images comprising simplified images or views of the one or more anatomical features of interest. That is, a projected image representation 18 on a subject 2 may be a simplified image or view only showing the one or more anatomical features most relevant to the application. Such a simplified image or view is typically a filtered, selective or schematic image or view only showing e.g. (parts of) blood vessels and/or perforators in case of the DIEP-flap procedure. Such a simplified image or view is less distracting and most efficient for providing relevant information to a user of the projection system 1.

FIGS. 3 and 4 each show examples of such an embodiment wherein a projected image representation 18 of one or more anatomical features only comprises features relevant to the application at hand, e.g. only blood vessels 5b and perforators 5a for a DIEP-flap procedure. In a further aspect, the present invention relates to a method for image projection of anatomical features on a subject, comprising providing one or more preoperative images of one or more anatomical features of interest using a medical imaging apparatus 8, each of the preoperative images comprising a plurality of preoperative position markers 4. In this method step raw anatomical feature information is obtained and represented in one or more preoperative images comprising a co-imaged plurality of preoperative position markers 4. The plurality of preoperative position markers 4 may be externally applied position markers suitable to be imaged by e.g. a CT or MM scanner. Alternatively, the plurality of preoperative position markers 4 may also be physiological markers such as scanned bone or tissue structures.

The method then comprises storing the one or more preoperative images into an image storage unit. This allows central access to all of the one or more preoperative images captured with the medical imaging apparatus and may facilitate fast image processing, typically using specialised software. As such, the method then comprises post processing the stored one or more preoperative images into one or more image representations 18 comprising simplified images or views (e.g. filtered, selective or schematic) of the one or more anatomical features of interest. In this step raw anatomical feature information is typically filtered for only the one or more anatomical features relevant to the application at hand, e.g. blood vessels 5b and perforators 5a as depicted in FIGS. 3 and 4.

At this point one or more image representations 18 of one or more relevant anatomical features is available for image projection purposes. The method now comprises disposing a plurality of intraoperative position markers 10 on the first body surface 6 of the subject 2 at the same location as the plurality of preoperative position markers 4. Note that the preoperative position markers 4 may be replaced by the intraoperative position markers 10 in certain situations. For example, when a CT scanner is used for obtaining preoperative images, the plurality of preoperative position markers 4 often comprise preoperative position markers made of lead for optimal contrast. Such lead markers 4 may not be suitable to be detected by e.g. a digital camera, infra red camera and/or RFID transmitter. Specialised intraoperative position markers 10 are thus sometimes needed for accurate image alignment onto the subject 2. In typical embodiments, the method comprises disposing at least three intraoperative position markers 10 on the first body surface 6 of the subject 2 at the same location as the plurality of preoperative position markers 4, i.e. three preoperative position markers 4.

The method further comprises detecting the plurality of intraoperative position markers 10 intraoperatively using a movable first detector 12 having a detection line of sight. Movable detection of the intraoperative position markers 10 is advantageous as it provides greater flexibly in how detection is carried out physically. That is, the detection of the intraoperative position markers 10 is independent from a detection angle, direction and/or movement and non-stationary detection is possible.

Further, the method comprises registering the detected plurality of intraoperative position markers 10 with the plurality of preoperative position markers 4 in each of the one or more image representations 18. This step enables registration and alignment of the one or more image representations 18 with the first body surface 6 of the subject 2, i.e. with respect to physical locations of the one or more anatomical features of interest.

The method then comprises projecting, substantially parallel to the detection line of sight, the one or more image representations 18 on a second body surface 20 intraoperatively using a movable projector 16 having a projection line of sight. Projecting the one or more image representations 18 comprises real-time image projection independent from synchronized movement of the first detector 12 and the projector 16. This method step is particularly advantageous as the detection and projection occurs synchronously in a movable fashion. In particular, a varying detection and projection angle of the first detector 12 and projector 16, wherein the first detector 12 and projector 16 move in unison, does not interfere with the projected image alignment as well as focussed image projection.

In a particular inventive embodiment, the method further comprises detecting motion of the subject 2, using e.g. a second detector 13, and dynamically projecting the one or more image representations 18 comprising the motion of the one or more anatomical features of interest in real-time. In some situations accurate image projecting of the one or more image representations 18 may not be guaranteed when one or more intraoperative position markers 10 are undetectable by the first detector 12. In such situations it may be advantageous to halt or stop image projection to prevent inaccurate or even erroneous projection of the one or more image representations 18. To that end, in an embodiment the method may further comprise stopping image projection of the one or more image representations 18 when one or more intraoperative position markers 10 lie outside a predetermined range of the detection line of sight of the first detector 12.

This embodiment may be advantageous when e.g. the first detector 12 and projector 16 point away from the subject 2, or the subject 2 itself blocks detection of one or more intraoperative position markers 10.

In a further embodiment the method may comprise stopping image projection of the one or more image representations 18 when each of the plurality of intraoperative position markers 10 are in the detection line of sight of the first detector 12 and wherein the detection line of sight lies outside a predetermined detection range. As mentioned earlier, it may be advantageous to only allow for image projection for a predetermined range of positions and/or orientations/angles of the first detector 12. This predetermined range can be made arbitrarily small and narrow so that the projector 16 only projects anatomical features when the first detector 12 detects the subject 2 through a small "key hole" whilst all intraoperative position markers 10 are detected by the first detector 12.

In addition to the above scenario, it is also possible that each of the plurality of intraoperative position markers 10 are in fact detectable by the first detector 12 but the one or more anatomical features to be projected may be blocked by secondary or further anatomical features. That is, secondary or further anatomical features may block physical access to the one or more anatomical features of interest should intervention, e.g. medical intervention, be necessary. As explained above for the projection system, secondary or further anatomical features may be sensitive nerve bundles, fat structures etc. overlaying or covering the one or more anatomical features to be projected, thereby blocking access thereto should intervention be necessary.

In view of the above, the method may further comprise stopping image projection of the one or more image representations 18 when each of the plurality of intraoperative position markers 10 are in the detection line of sight of the first detector 12 and when a secondary anatomic feature is interposed between the one or more anatomic features to be projected and the first projector 12 along the detection line of sight thereof.

This embodiment is also advantageous for e.g. "key hole" projections wherein projections of one or more anatomical features is stopped for positions and/or orientations/angles of the first detector 12 outside a predetermined range. In this way it is possible to prevent projection of the one or more anatomical features of interest when intermediate anatomical features are interposed between anatomical features of interest and the first detector 12 along the detection line of sight thereof. Such "key hole" projections ensure that anatomical features of interest are readily accessible and not blocked from access should intervention be necessary.

The present invention embodiments have been described above with reference to a number of exemplary embodiments as shown in the figures. It is readily understood that various medical and non-medical applications of the disclosed projection system 1 and method is conceivable. For example, as mentioned earlier, the projection system 1 of the present invention may be used for a deep inferior epigastric perforator (DIEP) reconstruction procedure. As an extension and generalisation of "DIEP", the projection system 1 may in fact be used for any surgical procedures using "flaps" or parts of body tissue for transplantation purposes, wherein one or more blood vessels are accurately projected on the subject for identifying parts of body tissue that are oxygenated by the one or more projected blood vessels.

Further use of the projection system 1 could be jaw (mandibula) reconstruction by excising a suitable bone part comprising blood vessels from e.g. a lower leg, wherein the blood vessels are projected by the projection system 1.

An even further use of the projection system 1 could be accurately projecting a location of a tumour for radiation therapy. In particular, real-time (breathing) motion of a lung tumour can also be accurately projected by the projection system 1. Projected image representations of such a moving lung tumor may provide additional information for radiation therapy. A plurality of preoperatively tattooed position markers may then be used as intraoperative position markers.

An even further use of the projection system 1 could be a face lift procedure, wherein one or more nerves are projected onto the face of the subject to prevent damage to the one or more nerves during surgery.

Modifications and alternative implementations of some parts or elements is therefore possible, and are included in the scope of protection as defined in the appended claims.

The invention claimed is:

1. A projection system for image projection of anatomical features on a subject, comprising
a plurality of intraoperative position markers (10) removably disposed on a first body surface (6);

a moveable first detector (12) for intraoperative detection of the plurality of intraoperative position markers (10) and having a detection line of sight; and a control unit (14) arranged for receiving one or more preoperative images comprising one or more anatomical features of interest, each of the preoperative images comprising a plurality of preoperative position markers (4), wherein the control unit (14) is further arranged for registering the detected plurality of intraoperative position markers (10) with the plurality of preoperative position markers (4) in each of the preoperative images;

the projection system (1) further comprising a movable projector (16) having a projection line of sight and being configured for projecting an image representation (18) of the one or more anatomical features of interest on a second body surface (20), the projection line of sight being substantially parallel to the detection line of sight, the projected image representation (18) being based on the one or more preoperative images and the registered plurality of intraoperative position markers (10) with the plurality of preoperative position markers (4), wherein the control unit (14) is in communication with the first detector (12) and projector (16) and arranged for real-time image projection of the image representation (18) on the second body surface (20) by the projector (16) independent from synchronized movement and varying detection and projection angles of the first detector (12) and the projector (16).

2. The projection system according to claim 1, wherein the projected image representation (18) is a static image projection.

3. The projection system according to claim 1, comprising a second detector (13) configured for intraoperative detection of motion of the subject (2), wherein the control unit (4) is in further communication with the second detector (13) and arranged for dynamically projecting the image representation (18) in real-time, the projected image representation (18) comprising the motion of the one or more anatomical features of interest.

4. The projection system according to claim 3, wherein the second detector (13) is configured for intraoperative detection of heart and/or breathing motion of the subject (2).

5. The projection system according claim 1, wherein the projector (16) is a laser projector.

6. The projection system according to claim 1, wherein the first detector (12) and the projector (16) are disposed in a portable handheld housing (17).

7. The projection system according to claim 1, wherein the first detector (12) comprises a digital camera and each of the plurality of intraoperative position markers (10) comprises a visual position marker.

8. The projection system according to claim 1, wherein the first detector (12) comprises an infra red camera and each of the plurality of intraoperative position markers (10) comprises a heat or cold source.

9. The projection system according to claim 1, wherein the first detector (12) comprises an RFID receiver and each of the plurality or intraoperative position markers (10) comprises an RFID transmitter.

10. The projection system according to claim 1, comprising at least three intraoperative position markers (10).

11. The projection system according to claim 1, wherein each of the intraoperative position markers (10) comprises a plurality of rectangular and/or square bar markers.

12. The projection system according to claim 1, wherein the second body surface (20) comprises an internal body surface.

13. The projection system according to claim 1, wherein the control unit (14) is further arranged to stop image projection of the image representation (18) when one or more intraoperative position markers (10) lie outside a predetermined range of the detection line of sight of the first detector (12).

14. The projection system according to claim 1, wherein the control unit (14) is arranged to stop image projection of the image representation (18) when each of the plurality of intraoperative position markers (10) are in the detection line of sight of the first detector (12) and wherein the detection line of sight lies outside a predetermined detection range.

15. The projection system according to claim 1, wherein the control unit (14) is arranged to stop image projection of the image representation (18) when each of the plurality of intraoperative position markers (10) are in the detection line of sight of the first detector (12) and when a secondary anatomic feature is interposed between one or more anatomic features to be projected and the first detector (12) along the detection line of sight thereof.

16. Use of the projection system according to claim 1 for a deep inferior epigastric perforator (DIEP) reconstruction procedure.

17. A method for image projection of anatomical features on a subject, comprising providing one or more preoperative images of one or more anatomical features of interest using a medical imaging apparatus (8), each of the preoperative images comprising a plurality of preoperative position markers (4);

storing the one or more preoperative images into an image storage unit;

post processing the stored one or more preoperative images into one or more image representations (18) comprising simplified images or views of the one or more anatomical features of interest;

disposing a plurality of intraoperative position markers (10) on the first body surface (6) of the subject (2) at the same location as the plurality of preoperative position markers (4);

detecting the plurality of intraoperative position markers (10) intraoperatively using a movable first detector (12) having a detection line of sight;

registering the detected plurality of intraoperative position markers (10) with the plurality of preoperative position markers (4) in each of the one or more image representations (18);

projecting substantially parallel to the detection line of sight the one or more image representations (18) on a second body surface (20) intraoperatively using a movable projector (16) having a projection line of sight, wherein projecting the one or more image representations (18) comprises real-time projection independent from synchronized movement and varying detection and projection angles of the first detector (12) and the projector (16).

18. The method according to claim 17, further comprising detecting motion of the subject (2) using a second detector (13), and dynamically projecting the one or more image representations (18) comprising the motion of the one or more anatomical features of interest in real-time.

19. The method according to claim 17, further comprising stopping image projection of the one or more image representations (18) when one or more intraoperative position markers (10) lie outside a predetermined range of the detection line of sight of the first detector (12).

20. The method according to claim 17, further comprising stopping image projection of the one or more image representations (18) when each of the plurality of intraoperative position markers (10) are in the detection line of sight of the first detector (12) and wherein the detection line of sight lies outside a predetermined detection range.

21. The method according to claim 17, further comprising stopping image projection of the one or more image representations (18) when each of the plurality of intraoperative position markers (10) are in the detection line of sight of the first detector (12), and when a secondary anatomic feature is interposed between the one or more anatomic features to be projected and the first projector (12) along the detection line of sight thereof.

\* \* \* \* \*